US011304987B2

(12) United States Patent
Azoulay et al.

(10) Patent No.: US 11,304,987 B2
(45) Date of Patent: Apr. 19, 2022

(54) ARGAN EXTRACTS FOR THE TREATMENT OF DERMATOLOGICAL CONDITIONS

(71) Applicant: FRE SKINCARE LTD, Tel Aviv (IL)

(72) Inventors: Michael Azoulay, Tel Aviv (IL); Mickael Bensadoun, Tel Aviv (IL); Sharon Rozenblat, Tel Aviv (IL)

(73) Assignee: FRE SKINCARE LTD, Tel Aviv (IL)

( * ) Notice: Subject to any disclaimer, the term of this patent is extended or adjusted under 35 U.S.C. 154(b) by 0 days.

(21) Appl. No.: 16/809,148

(22) Filed: Mar. 4, 2020

(65) Prior Publication Data
US 2020/0281999 A1    Sep. 10, 2020

Related U.S. Application Data

(60) Provisional application No. 62/813,912, filed on Mar. 5, 2019.

(51) Int. Cl.
| | |
|---|---|
| *A61K 36/00* | (2006.01) |
| *A61K 36/28* | (2006.01) |
| *A61K 31/047* | (2006.01) |
| *A61K 31/661* | (2006.01) |
| *A61K 31/192* | (2006.01) |
| *A61K 9/00* | (2006.01) |
| *A61Q 17/04* | (2006.01) |
| *A61P 17/06* | (2006.01) |
| *A61P 17/08* | (2006.01) |
| *A61K 35/02* | (2015.01) |
| *A61K 8/92* | (2006.01) |
| *A61K 8/9789* | (2017.01) |
| *A61P 17/10* | (2006.01) |

(52) U.S. Cl.
CPC .............. *A61K 36/28* (2013.01); *A61K 8/922* (2013.01); *A61K 8/9789* (2017.08); *A61K 9/0014* (2013.01); *A61K 31/047* (2013.01); *A61K 31/192* (2013.01); *A61K 31/661* (2013.01); *A61K 35/02* (2013.01); *A61P 17/06* (2018.01); *A61P 17/08* (2018.01); *A61P 17/10* (2018.01); *A61Q 17/04* (2013.01)

(58) Field of Classification Search
CPC ..................................................... A61K 36/00
USPC ........................................................ 424/725
See application file for complete search history.

(56) References Cited

U.S. PATENT DOCUMENTS

| | | |
|---|---|---|
| 3,755,560 A | 8/1973 | Dickert et al. |
| 4,421,769 A | 12/1983 | Dixon et al. |
| 5,658,247 A | 8/1997 | Henley |
| 5,667,487 A | 9/1997 | Henley |
| 2007/0224138 A1* | 9/2007 | Gibbons .............. A61K 8/9789 424/60 |

FOREIGN PATENT DOCUMENTS

CN             102670438 A    *   9/2012

* cited by examiner

*Primary Examiner* — Michael V Meller
(74) *Attorney, Agent, or Firm* — The Roy Gross Law Firm, LLC; Roy Gross

(57) ABSTRACT

The application provides compositions, in particular dermatological compositions comprising extracts from argan tree for the treatment and prevention of dermatological conditions. More particularly, a composition comprising argan oil (AO), argan leaf extract (AL) and argan stem cells (ASC) is provided. Further provided is a method for reducing photoaging of the skin of a subject due to exposure to UV radiation which comprises applying the composition of the invention to the subject prior to exposure to UV radiation.

14 Claims, 7 Drawing Sheets

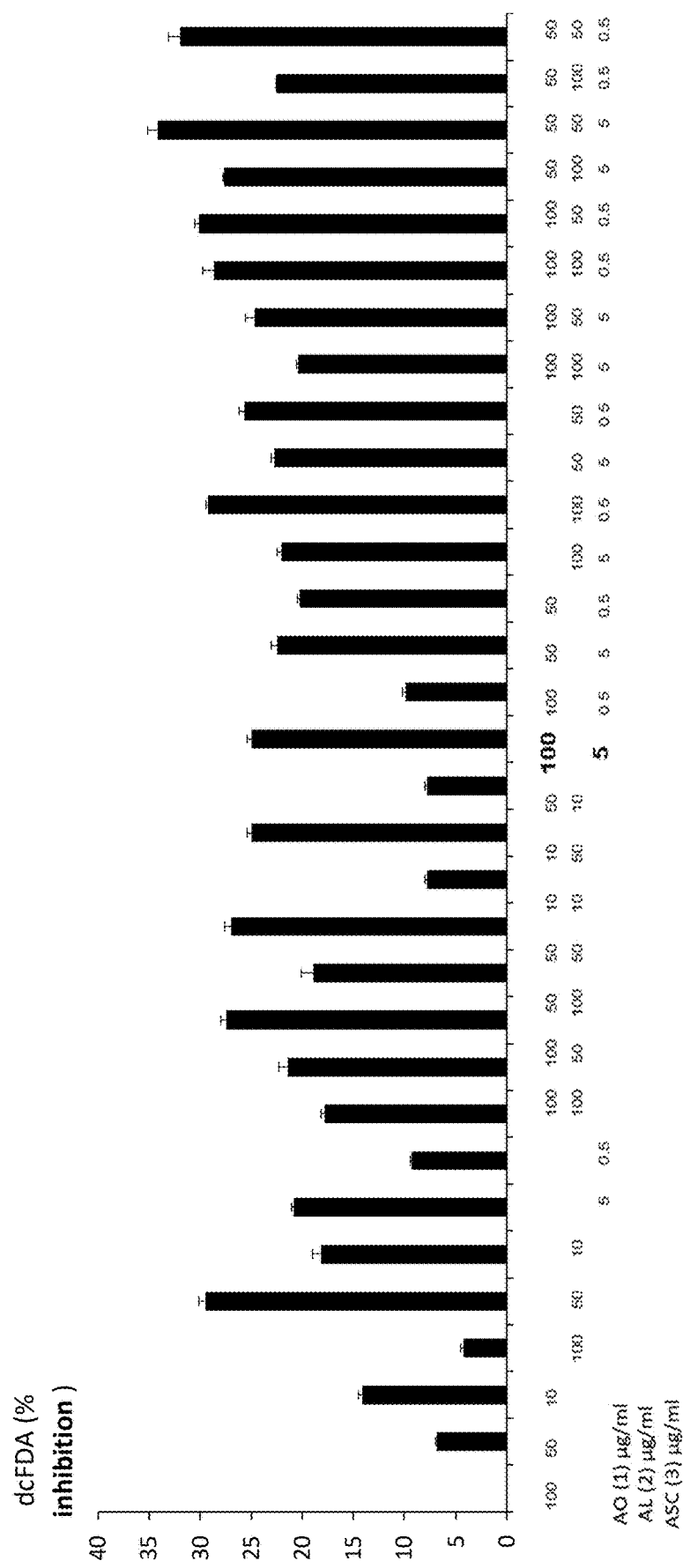

ARGAN EXTRACTS FOR THE TREATMENT OF DERMATOLOGICAL CONDITIONS

CROSS REFERENCE TO RELATED APPLICATIONS

This Application claims the benefit of and priority to U.S. Provisional Patent Application No. 62/813,912, filed Mar. 5, 2019 entitled ARGAN EXTRACTS FOR THE TREATMENT OF DERMATOLOGICAL CONDITIONS. The contents of the above application are incorporated by reference as if fully set forth in its entirety.

FIELD OF THE INVENTION

The application provides compositions, in particular dermatological compositions comprising extracts from argan tree for the treatment and prevention of dermatological conditions.

BACKGROUND OF THE INVENTION

Athletes that workout outdoor are more susceptible to environmental factors, such as ultra violet light (UV), pollution and the like. Further, sweat may increase the damage to the skin due to increased photosensitivity.

UV is the main cause to photoaging of the skin (contributes up to 80% of extrinsic aging) leading to free radicals, oxidative stress, depletion of antioxidants in the superficial epidermal layers, increased production of matrix metalloproteinases (MMPs) resulting in skin thickening, collagen and elasticity loss and wrinkle formation. UV could also cause inflammation.

One of the most important roles of the skin is to be an effective barrier between the internal and external environment. The skin serves as a barrier from pathogen, damage and fluid loss. The barrier function of the skin may be deteriorated in the dry environment or following UV radiation. This may lead to an increased water loss (transepidermal water loss, TEWL) that might result in reduced skin hydration.

The intensive use of air conditioners, long hot showers and overuse of soap might also aggravate dry skin.

After spending some hours under UV radiation, pollutant, dry weather, air conditions etc, the skin needs to recover its moisturization in order to strengthen its skin barrier function.

Thus, there is a need for a composition that will improve skin hydration, prevents water loss and restores skin barrier that will have an antioxidant activity and/or anti-inflammatory effect and will protect the skin from photoaging and UV-induced skin damage.

SUMMARY OF THE INVENTION

In some embodiments of the invention, there is provided a composition comprising argan oil (AO), argan leaf extract (AL) and argan stem cells (ASC). In some embodiments of the invention, the composition is a topically applicable cosmetic/dermatological composition.

In some embodiments of the invention, the argan oil (AO), argan leaf extract (AL) and argan stem cells (ASC) form a mixture or a complex.

In some embodiments of the invention, the composition provided herein is for treating a dermatological condition, which may be without limitation, one or more of aging skin, UV radiation-induced skin damage, acne, skin allergy, eczema, atopic dermatitis, psoriasis, seborrhea and rocacea.

In some embodiments of the invention, the argan oil (AO) is a cold pressed extract from kernel.

In some embodiments of the invention, the argan leaf extract (AL) is a water Argania *Spinosa* Leaf Extract.

In some embodiments of the invention, the argan leaf extract (AL) is a glycerin Argania *Spinosa* Leaf Extract.

In some embodiments of the invention, the argan leaf extract (AL) is a water, glycerin and Argania *Spinosa* Leaf Extract.

In some embodiments of the invention, the argan stem cells (ASC) is Argania *Spinosa* Callus Culture Extract. In some embodiments of the invention, the extract further includes isomalt, lecithin (and) sodium benzoate and water.

In some embodiments of the invention, the combination of at least two of AO, ASC and AL has an antioxidative synergistic activity.

In some embodiments of the invention, the combination of AO and ASC has an antioxidative synergistic activity.

In some embodiments of the invention, the dermatological condition is one or more of skin condition associated with workout, sweat, dry skin, xerosis, UV damage, anti-aging, photo-aging, skin allergy, eczema, acne and a change on the skin pH.

In some embodiments of the invention, the combination of at least two of AO, ASC and AL has an anti-inflammatory synergistic activity.

In some embodiments of the invention, the composition is in a form of a cream, lotion, cleanser or serum.

In some embodiments of the invention, the composition is for a daily use.

In some embodiments of the invention, the ratio of AO:AL:ASC is AO:AL:ASC 1:1:0.01 or 1:1:0.005 or 1:2:0.01.

In some embodiments of the invention, the ratio between AO to ASC is about 1:0.05.

In some embodiments of the invention, the ratio between AO to AL is 10:1 to 1:10

In some embodiments of the invention, the ratio between AO to AL is different than 2:1.

In some embodiments of the invention, the ratio between AO to AL is different than about 2:1.

In some embodiments of the invention, the ratio between AO to AL is about 1:1 and the ratio between AO and ASC is 1:0.001 to 1:0.2.

In some embodiments of the invention, the ratio between AO to AL is about 1:1 and the ratio between AO and ASC is 1:0.001 to 1:0.1.

In some embodiments of the invention, the ratio between AO to AL is about 1:1 and the ratio between AO and ASC is 1:0.001 to 1:0.05

In some embodiments of the invention, the ratio between AO to AL is about 1:1 and the ratio between AO and ASC is 1:0.005 to 1:0.05.

In some embodiments of the invention, the ratio between AO to AL is about 1:1.

In some embodiments of the invention, the ratio between AO to AL is about 1:2.

In some embodiments of the invention, the ratio between AO to AL is about 1:2 and the ratio between AO and ASC is 1:0.001 to 1:0.1.

In some embodiments of the invention, the Argan oil (AO) is a cold pressed oil containing fatty acids, such as, palmitic acid (at least 2%), stearic acid (at least 1%), oleic acid (at least 15%), linoleic acid (at least 15%).

In some embodiments of the invention, the Argan leaf (AL) contains at least 5% argan leaf extract with at least 0.1% flavonoid content.

In some embodiments of the invention, the Argan Stem Cells (ASC) is Argania spinosa sprout cell culture that contains at least 40%, 45%, 50%, 55%, 60 or more of argan stem cell culture.

In some embodiments of the invention, Argan oil (AO) is a cold pressed oil containing fatty acids, such as, palmitic acid, stearic acid, oleic acid and linoleic acid.

In some embodiments of the invention, Argan leaf (AL) contains at least 10% argan leaf extract with flavonoid content, which may be at a concentration of at least 0.1%. In some embodiments of the invention, Argan stem cells is Argania spinosa sprout cell culture that contains 50% or more of argan stem cell culture. In some embodiments, Argania spinosa cell culture extract (dry) correspond to at least 50% argan stem cell culture, isomalt, phospholipids, sodium benzoate and water.

In some embodiments of the invention, Argan oil (AO) is a cold pressed oil containing fatty acids, such as, palmitic acid (10-15%), stearic acid (4-7.4%), oleic acid (43-50%) and linoleic acid (29-37%).

In some embodiments of the invention, Argan leaf (AL) contains at least 10% argan leaf extract with at least 0.3% flavonoid content. In some embodiments of the invention, Argan stem cells is Argania spinosa sprout cell culture that contains 50% of argan stem cell culture (Argania spinosa cell culture extract (dry) correspond to 50% cell culture 0.8%; 93% isomalt, phospholipids 0.8%, sodium benzoate 0.3% and water<6%).

In some embodiments of the invention, there is provided a method of treating one or more of aging skin, UV radiation-induced skin damage, acne, atopic dermatitis, xerosis, skin allergy, eczema, psoriasis, seborrhea and rosacea in a subject in need comprising the step of contacting the subject in need skin with the composition described herein.

In some embodiments of the invention, the step of contacting the subject in need skin with the composition described herein is performed before, during and/or after the exposure to the UV.

In some embodiments of the invention, the subject is an athlete who work out outdoor.

In some embodiments of the invention, there is provided a method for reducing photoaging of the skin of a subject due to exposure to UV radiation which comprises applying the composition described herein to the subject prior to exposure to UV radiation.

In some embodiments of the invention, there is provided a method for reducing photoaging of the skin of a subject due to exposure to UV radiation which comprises applying the composition described herein to the subject after the exposure to UV radiation.

In some embodiments of the invention, there is provided a method for reducing the occurrence of phototoxic or photoallergic reactions in a subject due to exposure to UV radiation which comprises applying the composition described herein to the subject prior to exposure to UV radiation.

In some embodiments of the invention, there is provided a method for reducing the occurrence of phototoxic or photoallergic reactions in a subject due to exposure to UV radiation which comprises applying the composition described herein to the subject after the exposure to UV radiation.

In some embodiments of the invention, the composition of the invention as described above further comprising one or more of anti acne substance (such as benzoyl peroxide, salicylic acid, retinoids, sulfur, antibiotic, azelaic acid), antiaging substances (such as vitamin C, vitamin E, reservatrol, antioxidants, vitamin A (retinols and its derivates (retinaldehyde and tretinoin)), peptides, hyaluronic acid, lactic acid glycolic acid, alpha hydroxyis), or SPF compounds such as inorganic compounds (such as zinc oxide, titanium dioxide, kaoline, iron oxide, calamine etc.) PABA derivates (such as octinoxate, salicylates, cinnamates etc.), broad spectrum filters (such as ecamsule, silatriazole, bemotrizinol, bisoctizole) or systemic filters (such as beta-carotene, ascorbic acid, tocopherols, retinol, green tea polyphenols, aspirin, PABA, selenium antihistamines and the like.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Test Items were incubated with DPPH. Results are presented as % of scavenging capacity in Mean±SEM; n=3.

Figure 1A:
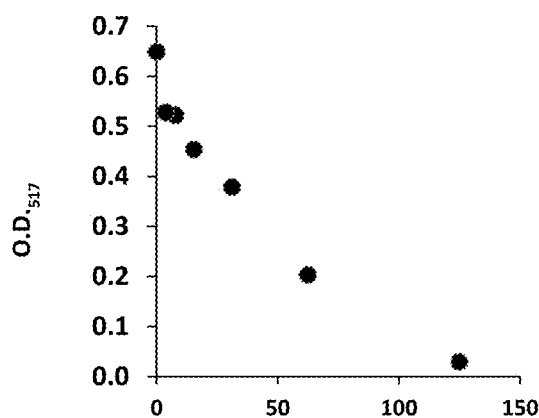
FIGS. 1A-1D depict the a-cellular antioxidant effect by measuring the ROS scavenging capacity of different concentrations of AL with or without 25 mg/ml AO or/and 25 mg/ml ASC (FIG. 1C), different concentration of AO with or without 25 mg/ml ASC (FIG. 1D) using a standard curve of the scavenging capacity of Trolox (FIGS. 1A and 1B) as measured by DPPH.
Figure 1B:
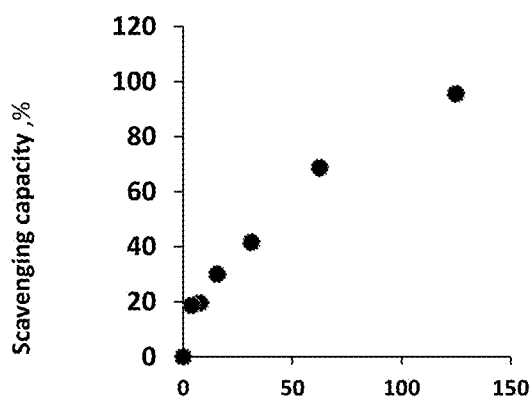
Figure 1C:
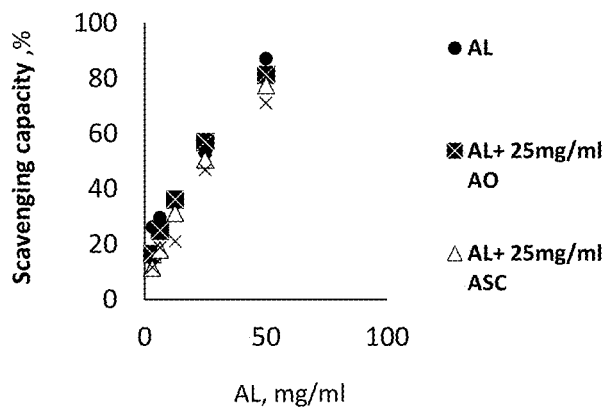
Figure 1D:
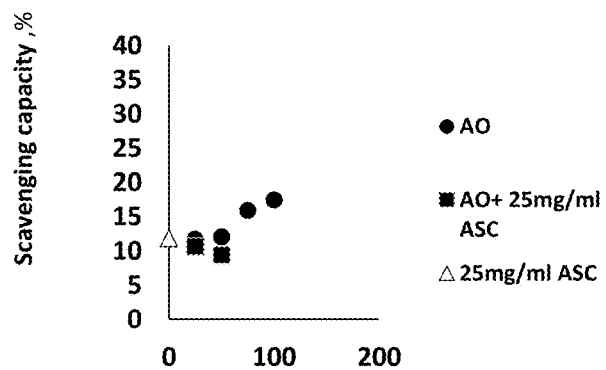
Figure 2A:
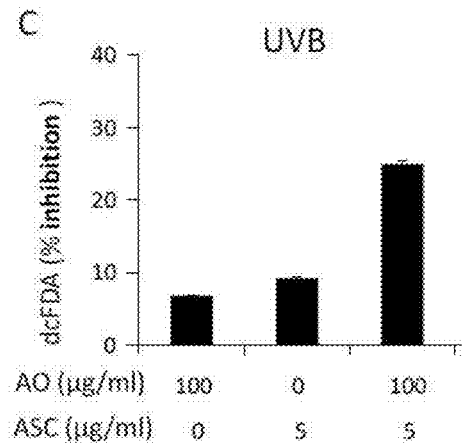
Figure 2B:
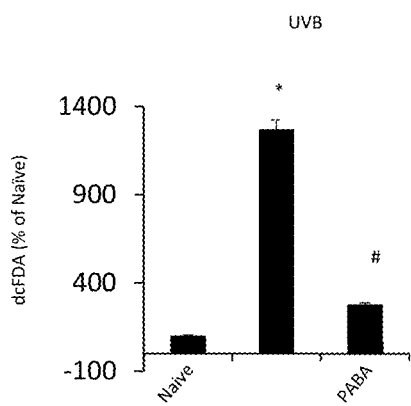

FIG. 2A and FIG. 2B depict the cellular antioxidant effect of argan oil (AO), argan leaf extract (AL) and argan stem cells (ASC) alone or together in various concentrations as measured by DCFDH (FIG. 2B). FIG. 2A is the control samples used in this study: naive cells, cells after UVB and positive control PABA. Synergistic effect of AO at concentration of 100 μg/ml and ASC at concentration of 5 μg/ml is presented in FIG. 2C. The test was performed in HaCaT cells whereas the amount of free radicals was detected following irradiation. PABA was used as a positive control. HaCaT cells were incubated with the Test Items for 24 hours, followed by exposure to UVB irradiation (20 mJ/cm2). PABA was added 15 min prior to irradiation. Following UVB exposure, cells were incubated with DCFDA for 30. Then plate was washed with PBS and measured fluorescently at ex 485 nm/em 535 nm. Results are presented as % of Naive for controls (A) and % of inhibition for Test Items (B). Results are presented in Mean±SEM; n=3.

Figure 3A:
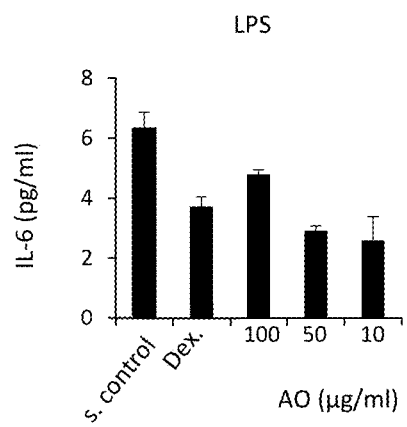
Figure 3B:
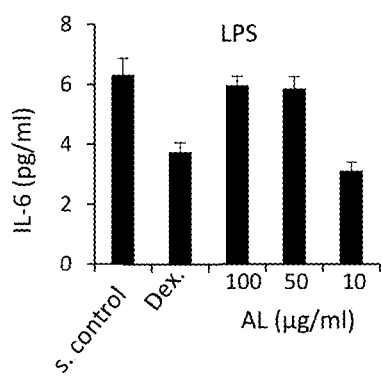
Figure 3C:
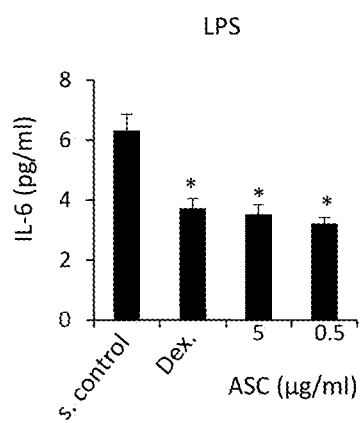

FIGS. 3A, 3B and 3C depict the anti-inflammatory effect of AO FIG. 3A), AL (FIG. 3B) and ASC (FIG. 3C) as measured by the ability of the test compounds to inhibit IL6 expression following LPS stimulation. HaCaT cells were seeded and treated with LPS (1 μg/ml) with or without the single Test Items and mixtures. Following 24 hours, IL-6 levels were measured by using commercial kit. IL-6 levels in the presence of AO (A), AL (B), ASC (C) are presented as Mean±SEM; n=3.

FIGS. 4A, 4B, 4C, 4D, 4E and 4F depict the anti-inflammatory effect of AO (FIG. 4A), AL (FIG. 4B) and ASC (FIG. 4C) or combination of AO and AL (FIG. 4D, FIG. 4F) or combination of AO, AL and ASC (FIG. 4E, FIG. 4F) as measured by the ability of the test compounds (FIG.

Figure 4A:
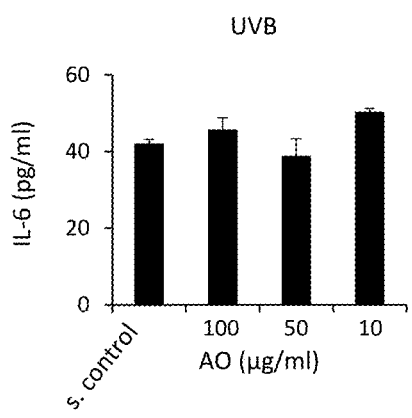
Figure 4B:
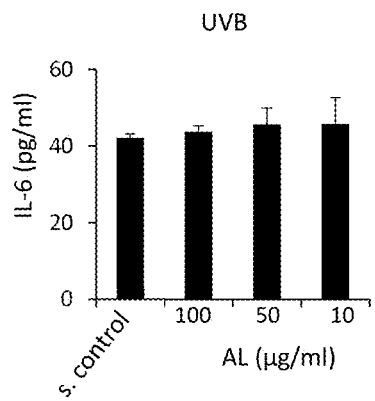
Figure 4C:
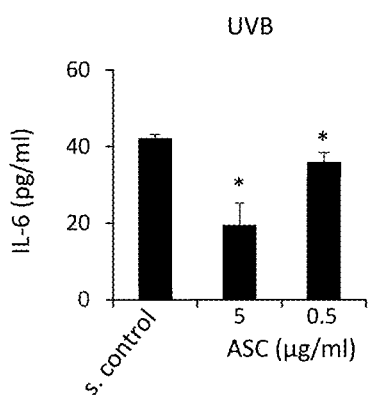

4 A, FIG. 4B and FIG. 4C) and their combinations (FIG. 4D, FIG. 4E and FIG. 4 F) to inhibit IL6 expression in Keratinocytes (HaCaT) cells following UVB irradiation. HaCaT cells were incubated with the Test Items for 24 hours, followed by exposure to UVB irradiation (20 mJ/cm2). PABA was added 15 min prior to irradiation. The levels of IL-6 (A, C, D, E, F) was measured in the spent media by using commercial kits. Results are presented in Mean±SEM; n=3.

DETAILED DESCRIPTION OF THE INVENTION

The invention is based on the surprising synergistic anti oxidative and anti-inflammatory effect that were identified in a composition comprising argan oil (AO), argan leaf extract (AL) and argan stem cells (ASC) in certain ratios therebetween.

Specifically, as is exemplified in the Examples section, AO, AL and ASC showed no effect or slight effect in the different tests when given alone, and when given in a combination, they showed a synergistic antioxidant or anti-inflammatory response. In some embodiments of the invention, there is provided a composition comprising argan oil (AO), argan leaf extract (AL) and argan stem cells (ASC). In some embodiments of the invention, the composition is topically applicable cosmetic/dermatological composition.

In some embodiments of the invention, the argan oil (AO), argan leaf extract (AL) and argan stem cells (ASC) form a complex.

In some embodiments of the invention, the composition provided herein is for treating a dermatological condition, which may be without limitation, one or more of aging skin, UV radiation-induced skin damage, xerosis, acne, atopic dermatitis, skin allergy, eczema, psoriasis, seborrhea and rocacea.

In some embodiments of the invention, the argan oil (AO) is a cold pressed extract from kernel.

In some embodiments of the invention, the argan leaf extract (AL) is a water, glycerin Argania *Spinosa* Leaf Extract.

In some embodiments of the invention, the argan stem cells (ASC) is a sprout cell cultures extract, with isomalt, lecithin, sodium benzoate and water.

In some embodiments of the invention, the combination of at least two of AO, ASC and AL has an antioxidative synergistic activity.

In some embodiments of the invention, the combination of AO and ASC has an antioxidative synergistic activity.

In some embodiments of the invention, the dermatological condition is one or more of skin condition associated with workout, sweat, dry skin, skin allergy, enhanced UV damage, aging, photoaging and a change on the skin pH.

In some embodiments of the invention, the combination of at least two of AO, ASC and AL has an anti-inflammatory synergistic activity.

In some embodiments of the invention, the composition is in a form of a cream, lotion, cleanser or serum.

In some embodiments of the invention, the composition is for a daily use.

In some embodiments of the invention, the ratio of AO:AL:ASC is AO:AL:ASC 1:1:0.01 or 1:1:0.005 or 1:2:0.01.

In some embodiments of the invention, the ratio between AO to ASC is about 1:005, 1:0.01 or 1:0.05.

In some embodiments of the invention, the ratio between AO to AL is 10:1 to 1:10 In some embodiments of the invention, the ratio between AO to AL is different than 2:1. In some embodiments of the invention, the ratio between AO to AL is different than about 2:1.

In some embodiments of the invention, the ratio between AO to AL is about 1:1 and the ratio between AO and ASC is 1:0.005 to 1:0.2.

In some embodiments of the invention, the ratio between AO to AL is about 1:1.

In some embodiments of the invention, there is provided a method of treating one or more of aging skin, UV radiation-induced skin damage, acne, xerosis, skin allergy, eczema, atopic dermatitis, psoriasis, seborrhea and rosacea in a subject in need comprising the step of contacting the subject in need skin with the composition described herein.

In some embodiments of the invention, the step of contacting the subject in need skin with the composition described herein is performed before and/or after the exposure to the UV.

In some embodiments of the invention, the subject is an athlete who work out outdoor.

In some embodiments of the invention, there is provided a method for reducing photoaging of the skin of a subject due to exposure to UV radiation which comprises applying the composition described herein to the subject prior to exposure to UV radiation.

In some embodiments of the invention, there is provided a method for reducing photoaging of the skin of a subject due to exposure to UV radiation which comprises applying the composition described herein to the subject after the exposure to UV radiation.

In some embodiments of the invention, there is provided a method for reducing the occurrence of phototoxic or photoallergic reactions in a subject due to exposure to UV radiation which comprises applying the composition described herein to the subject prior to exposure to UV radiation.

In some embodiments of the invention, there is provided a method for reducing the occurrence of phototoxic or photoallergic reactions in a subject due to exposure to UV radiation which comprises applying the composition described herein to the subject after the exposure to UV radiation.

The composition of the invention has a strong effect in improving skin hydration, prevention of water loss and restoration of skin barrier as well as in its antioxidant activity that protects the skin from photoaging.

Further, the composition has potent anti-oxidant and hydrating effects.

In some embodiments of the invention, the composition is suitable as anti-pollution composition, it prevents photoaging and wrinkles, protects against UVB-induced oxidative stress and improves the antioxidative capacity of the skin.

In some embodiments of the invention, the composition rejuvenates the skin and prevents skin aging by, for example, protecting from photoaging, reducing oxidative stress and restores the skin's natural protective layer.

The invention will be further described by means of the following examples, which are not intended to limit the invention, as defined by the appended claims, in any manner.

According to some embodiments of the invention, the composition is a pharmaceutical composition and comprises a pharmaceutically acceptable carrier or diluent.

According to some embodiments of the invention, the composition is a cosmetic composition and comprises a cosmetically acceptable carrier or diluent.

According to some embodiments of the invention, the cosmetically acceptable carrier or diluent is formulated in a form selected from the group consisting of a cream, a gel, a spray, a lotion, an ointment, an oil, a wash, a shampoo, a soap and a spray.

Thus, according to one aspect of the present invention there is provided a method of treating and/or preventing and/or reducing UV skin damage in a subject in need thereof, the method comprising administering to the subject a therapeutically effective amount of each of the compositions which comprise plant extracts or active ingredient thereof as listed below, thereby treating and/or preventing and/or reducing UV skin damage in the subject.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

According to some embodiments of the invention, the unit dosage form further comprises AO extract at a concentration of about 0.5-50% weight/weight.

According to some embodiments of the invention, the unit dosage form further comprises AO extract at a concentration of about 0.5, 1, 5, 10, 15, 20, 25, 30, 3, 40, 45 or 50% weight/weight.

According to some embodiments of the invention, the unit dosage form further comprises AL extract at a concentration of about 0.5-50% weight/weight.

According to some embodiments of the invention, the unit dosage form further comprises AL extract at a concentration of about 0.5, 1, 5, 10, 15, 20, 25, 30, 3, 40, 45, or 50% weight/weight.

According to some embodiments of the invention, the unit dosage form further comprises ASC extract at a concentration of about 0.001-1% weight/weight.

According to some embodiments of the invention, the unit dosage form further comprises ASC extract at a concentration of about 0.001, 0.0025, 0.005, 0.0075, 0.1, 0.25, 0.5, 0.75 or 1% weight/weight.

According to some embodiments of the invention, the administering is effected at least once a day.

The present formulation may be combined with anti acne substances (such as benzoyl peroxide, salicylic acid, retinoids, sulfur, antibiotic, azelaic acid), antiaging substances (such as vitamin C, vitamin E, reservatrol, antioxidants, Vitamin A (retinols and its derivates (retinaldehyde and tretinoin)), peptides, Hyaluronic acid, lactic acid glycolic acid, alpha hydroxyis), SPF compounds such as Inorganic compounds (such as zinc oxide, Titanium dioxide, Kaoline, Iron oxide, Calamine etc) PABA derivates (such as Octinoxate, Salicylates, Cinnamates etc), Broad spectrum Filters (such as Ecamsule, Silatriazole, Bemotrizinol, Bisoctizole etc) or systemic filters (such as, beta-carotene, ascorbic acid, tocopherols, retinol, green tea polyphenols, aspirin, PABA, selenium antihistamines etc), In addition to the pharmaceutically effective amount of an agent disclosed herein, the compositions of this aspect of the present invention also include a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals.

In order to enhance the percutaneous absorption of the active ingredients (e.g., plant extracts of the present invention), one or more of a number of agents can be added to the pharmaceutical compositions including, but not limited to, dimethylsulfoxide, dimethylacetamide, dimethylformamide, surfactants, azone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray or an aerosol.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Examples of suitable emulsifiers are described in, for example, U.S. Pat. No. 3,755,560, issued to Dickert, et al. Aug. 28, 1973; U.S. Pat. No. 4,421,769, issued to Dixon, et al., Dec. 20, 1983; and McCutcheon's Detergents and Emulsifiers, North American Edition, pages 317-324 (1986), each of which is fully incorporated by reference in its entirety.

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form.

The compositions of the present invention can be formulated in any of a variety of forms utilized by the pharmaceutical or cosmetic industries for skin application including solutions, lotions, sprays, creams, ointments, salves, gels, oils, wash, shampoos, conditioners etc., as further described below.

The pharmaceutical compositions of the present invention may be formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The compositions of the subject invention, including but not limited to lotions and creams, may comprise a dermatologically acceptable emollient. As used herein, "emollient" refers to a material useful for the prevention or relief of dryness, as well as for the protection of the skin. Wide varieties of suitable emollients are known and may be used herein. See, e.g., Sagarin, Cosmetics, Science and Technology, 2nd Edition, Vol. 1, pp. 3243 (1972), which contains numerous examples of materials suitable as an emollient and is fully incorporated herein by reference. An exemplary emollient is glycerin. Additional emollients which may be used include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, lauric, isostearic, palmitic, and the like. Emollients also include fatty alcohols having ten to twenty carbon atoms, such as cetyl, myristyl, lauryl, isostearyl, stearyl and the like.

The composition of the present invention may also include additional components which are added, for example, in order to enrich the compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, *eucalyptus* oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

As mentioned above, the compositions of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonophoresis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

It will be appreciated that compositions of the present invention can be used in combination with other currently practiced therapies such as, without being limited to, SPF compounds and antibiotic therapy (e.g. local or systemic).

In some embodiments of the invention, the composition which comprises AO, AL and ASC further comprises one or more of the following:

In some embodiments of the invention, there is provided a composition comprising one or more of Water, Argan (Argania *Spinosa*) extract, acetyl hexapeptide-8, Xylitylglucoside, Hyaluronic Acid, Argan (Argania *Spinosa*) Oil, Coco Caprylate/Caprate, Glyceryl Stearate, Cetearyl Glucoside, Polysilicone-11, Isomalt, Dimethicone, Niacinamide, Laureth-12, Copper Tripeptide-1, Sweet Almond (*Prunus Amugdalus Dulcis*) Oil, Cetyl Alcohol, Saccharide Isomerate, Xanthan Gum, Anhydroxylitol, Xylitol, Argania *Spinosa* Callus Culture Extract, Tocopherol, Lecithin, Levulinic Acid, p-Anisic Acid, Sodium Benzoate, Geranium (*Pelargonium*) *Graveolens* Flower Oil, *Mentha Piperita* (Peppermint)Oil, Lavender (*Lavandula Angustifolia*) Oil, Ylang-Ylang (*Cananga Odorata*) and flower Oil.

According to some embodiments of the invention, there is provided a composition comprising water, ethylhexyl methoxycinnamate, glycerin, potassium cetyl phosphate, Argania *Spinosa* Kernel Oil, titanium Dioxide & trimethoxycaprylylsilane, cyclopentasiloxane, glyceryl Myristate, propanediol, behenyl Alcohol, caprylic/capric triglyceride, microcrystalline cellulose & cellulose gum, glycerin & sodium lactate & lactic acid & TEA-lactate & serine & urea & sorbitol & sodium chloride & allantoin, ascorbyl glucoside, phenoxyethanol & ethylhexylglycerin, Argania *Spinosa* Leaf Extract & maltodextrin, dimethicone, ammonium acryloyldimethyltaurate/VP Copolymer, mica, butylene Glycol & pentylene glycol & hydroxyphenyl propamidobenzoic acid, triethanolamine, allantoin, *cinnamomum camphora* linalooliferum wood oil, disodium EDTA, bisabolol, tocopheryl acetate (Vitamin E), carnosine, hyaluronic Acid, *Chamomilla Recutita* (*Matricaria*) Flower Extract, *Melissa Officinalis* Leaf Extract, Aspalathus *Linearis* (Rooibos) Leaf Extract, *Tilia* Vulgaris (Linden Blossom) Flower Extract According to some embodiments of the invention, there is provided a composition comprising comprising Water, Caprylic/Capric Triglyceride, Kaolin, Stearic Acid, Glycerin, Silica, Titanium Dioxide, Cetyl Alcohol, Glyceryl Stearate, Argan (Argania *Spinosa*) Water Extract, Argan (Argania *Spinosa*) Organic Oil, *Chamomilla Recutita* (*Matricaria*) Flower, Plantain (*Plantago Major*), Calendula (*Calendula Officinalis*) Flower, Dandelion (*Taraxacum Officinalis*) Leaf, Yarrow (*Achillea Millefolium*) Extract, Salicilyc Acid, Lactic Acid, Levulinic Acid, Azulen, p-Anisic Acid, Sodium Hydroxide, Argania *Spinosa* Sprout Cell Extract & Isomalt & Lecithin & Sodium Benzoate, Tocopheryl Acetate, Xanthan Gum, Panthenol, Allantoin, Dead Sea Salt, Lemongrass (Cymbopogon Schoenanthus) Oil, Bitter Orange (Citrus Aurantium *Amara*) Oil, Lavender (*Lavandula Angustifolia*) Oil.

In some embodiments of the invention, the composition of the invention restores skin barrier function, and is effective as anti-pollution, photoaging and wrinkles prevention.

In some embodiments of the invention, the composition of the invention further includes one or more of anti acne substance (such as benzoyl peroxide, salicylic acid, retinoids, sulfur, antibiotic, azelaic acid), antiaging substance (such as vitamin C, vitamin E, reservatrol, antioxidants, vitamin A (retinols and its derivates (retinaldehyde and tretinoin)), peptides, hyaluronic acid, lactic acid glycolic acid, alpha hydroxyis), or SPF compound such as inorganic compounds (such as zinc oxide, titanium dioxide, kaoline, iron oxide, calamine etc) PABA derivates (such as octinoxate, salicylates, cinnamates etc), broad spectrum filters (such as ecamsule, silatriazole, bemotrizinol, bisoctizole) or systemic filters (such as beta-carotene, ascorbic acid, tocopherols, retinol, green tea polyphenols, aspirin, PABA, selenium antihistamines and the like.

In some embodiments of the invention, the composition of the invention, which comprises AO, AL and ASC has strong anti-inflammatory activity and further at least two of the ingredients have synergistic anti-inflammatory activity.

In some embodiments of the invention, the synergistic anti-inflammatory activity of the at least two of AO, AL and ASC is observed following UV radiation.

In some embodiments of the invention, AO, AL and ASC reduce the expression of IL6 following UV radiation.

In some embodiments of the invention, the compositions may contain AO, AL and ASC and the ingredients provided according to the Tables below.

TABLE 1

|  | activity |
|---|---|
| Kaolin | Removes excess oil from the skin |
| Glycerin | Retains moisture and improves skin hydration |
| AO, AL, ASC | potent anti-oxidants and hydrating effects, reduces the signs of aging, improves the skin firmness and restores its elasticity |
| Chamomilla Recutita (Matricaria) Flower | Soothes and calms the skin, anti-allergenic properties |
| Plantain (Plantago Major) | Soothes and calms the skin |
| Calendula (Calendula Officinalis) Flower | Soothes and calms the skin, anti-inflammatory activity |
| Dandelion (Taraxacum Officinalis) Leaf | Prevents skin aging by reducing oxidative stress |
| Yarrow (Achillea Millefolium) Extract | Reduces skin inflammation and irritation |
| Salicilyc Acid | Accelerates the shedding of dead skin cells |
| Lactic Acid | Alpha Hydroxy Acid (AHA): improves the overall look and feel of the skin. Helps to remove dead skin cells and keeps the skin moisturized |
| Tocopheryl Acetate | Vitamin E, anti-oxidant |
| Panthenol | Soothes skin, reduces redness and irritation Restores the skin's natural protective layer |
| Allantoin | Calms irritated skin |
| Lemongrass (Cymbopogon Schoenanthus) Oil | Calms the skin, anti-bacterial |
| Bitter Orange (Citrus Aurantium Amara) Oil | Refreshing and balancing oily skin |
| Lavender (Lavandula Angustifolia) Oil | Calms and soothes the skin, anti-inflammatory properties |
| Yarrow (Achillea Millefolium) Extract | Reduces skin inflammation and irritation |

TABLE 2

| Octinoxate | UV filter |
|---|---|
| Titanium Dioxide | Ultraviolet Light Absorber |
| Glycerin | Retains moisture and improves skin hydration |
| AO, AL, ASC | Argan (Again Spinosa) Water Extract, Argan (Argania Spinosa) Organic Oil: potent anti-oxidants and hydrating effects, reduces the signs of aging, improves the skin firmness and restores its elasticity |
| Lactic Acid | Alpha Hydroxy Acid (AHA): improves the overall look and feel of the skin. Helps to remove dead skin cells and keeps the skin moisturized |
| Urea | Increases the water content of the top layers of the skin |
| Allantoin | Calms irritated skin |
| Ascorbic Acid | Vitamin C, antioxidant |
| Bisabolol | Calms irritation (German chamomile) |
| Tocopheryl Acetate | Vitamin E, anti-oxidant |
| Carnosine | Dipeptide (two amino acids: alanine and histidine). Works as an antioxidant and anti-inflammatory agent. |
| Hyaluronic Acid | Retains moisture by promoting skin hydration and by reducing trans-epidermal water loss (TEWL) |
| Chamomilla Recutita (Matricaria) Flower | Soothes and calms the skin, anti-allergenic properties |
| Tilia Vulgaris (Linden Blossom) Flower Extract | Soothes and hydrates the skin |
| Aspalathus Linearis (Rooibos) Leaf Extract, | Anti-aging properties due to its powerful antioxidant properties (flavonoids) |
| Melissa Officinalis Leaf Extract | Calms the skin, antioxidant |

TABLE 3

| Ingredient | activity |
|---|---|
| AO, AL, ASC | Potent anti-oxidants and hydrating effects, reduces the signs of aging, improves the skin firmness and restores its elasticity |
| Acetyl Hexapeptide-8 | A peptide compound that is used to reduce the appearance of wrinkles |
| Xylitylglucoside | Improves skin moisturization by preventing water loss |
| Hyaluronic Acid | Retains moisture by promoting skin hydration and by reducing trans-epidermal water loss (TEWL) |
| Coco-Caprylate/Caprate | A natural moisturiser, provides high hydration |
| Niacinamide | Vitamin B3, enhances the appearance of dry or damaged skin by reducing flaking and restoring suppleness |
| Copper tripeptide 1 | Stimulates the production of several important skin ingredients (e.g. collagen, elastin, and glycosaminoglycans). It has significant anti-inflammatory and antioxidant effect. Improve skin elasticity, clarity, firmness and reduce lines and wrinkles |
| Saccharide Isomerate | A water-binding agent and emollient, particularly helpful for dry skin |
| Tocopherol | Vitamin E, anti-oxidant |

EXAMPLES

Reference is now made to the following examples, which together with the above descriptions, illustrate the invention in a non-limiting fashion. The following experiments were conducted with Argan oil (AO), Argan leaf (AL) and Argan stem cells (ASC), as well as with various combinations thereof and a complex including Argan oil (AO), Argan leaf (AL), Argan stem cells (ASC).

The complex is a combination of three ingredients:
ARGAN OIL (AO) Cold pressed DE-OKO-001 (Company: Gustavheess): a cold pressed extract from kernel.

Argan leaf extract (AL): Arganyl LS 9781 (Company BASF): awater glycerin and Argania *Spinosa* Leaf Extract Argan stem cells (ASC) PhytoCell Tec Argan (Company: mibelle group):): a sprout cell cultures extract, isomalt, lecithin, sodium benzoate and water.

In the following experiments. the ingredients were added separately at a specific ratio described herein to a formulation.

Example 1

Anti-Oxidative Activity Measured by DPPH: DPPH: (2,2-Diphenyl-1-Picryl-Hydrazyl-Hydrate) Measurement of the Scavenging Capacity of Antioxidants Towards the Stable Free Radical DPPH. Trolox Calibration Curve was Used for Comparison.

ROS scavenging capacity of the Test items (AO, AL, ASC alone or in combinations) was evaluated a cellularly, by the DPPH method. The three (3) Test items were included in this assay. The assay was carried out in triplicates. The Test items (final volume of 20 µl for each concentration) were added to 380 µL of DPPH working solution. A blank control group (untreated working solution) and a vehicle control group was also examined.

Concomitantly, Trolox was added similarly to the DPPH working solution in order to generate the calibration curve. The solution was mixed thoroughly for 1 min.

After 30 min incubation period at RT in reduced light condition, the absorbance of 100 µL aliquots was measured by spectrophotometer (517 nm).

The scavenging efficacy was determined in the linear range of the curve, as written below:

Scavenging efficacy=(O.D.vehicle−O.D.treatment)
*100/O.D.vehicle

As can be seen from FIG. 1 (All three Test Items exhibited ROS scavenging activity depending on their concentration (FIG. 1) in the a-cellularly DPPH method. While ASC showed a very modest activity, equivalent to 20 µM Trolox, AO and AL exhibited moderate and strong anti-oxidant activity, respectively.

No anti-oxidant synergistic effect between compounds was shown when AL, AO and ASC were administered together in the a-cellularly DPPH method.

Example 2

Anti-Oxidant Activity Measured by DCFDA

DCFDA is a Cellular Reactive Oxygen Species (ROS) Assay Kit that uses the cell permeant reagent 2',7'-dichlorofluorescin diacetate (DCFDA, also known as H2DCFDA), a fluorogenic dye that measures hydroxyl, peroxyl and other reactive oxygen species (ROS) activity within the cell.

After diffusion in to the cell, DCFDA/H2DCFDA is deacetylated by cellular esterases to a non-fluorescent compound, which is later oxidized by ROS into 2', 7'-dichlorofluorescein (DCF). DCF is a highly fluorescent compound, which can be detected by fluorescence spectroscopy with excitation/emission at 495 nm/529 nm.

FIGS. 2A, 2B and 2C show the anti-oxidant efficacy in HaCaT cells following treatment with AO, AL, ASC and their combinations. HaCaT cells were incubated with the Test Items (AO, AL, ASC alone or in combinations) for 24 hours, followed by exposure to UVB irradiation (20 mJ/cm2). PABA was added 15 min prior to irradiation. Following UVB exposure, cells were incubated with DCFDA for 30 min. The plate was then washed with PBS and measured fluorescently at ex 485 nm/em 535 nm. Results are presented as % of Naive for controls (A) and % of inhibition for Test Items (B). Synergistic effect of AO and ASC is presented in (C). Results are presented in Mean±SEM; n=3.

Synergistic activity of AO and ASC was shown in the DCFDA test (FIG. 2C)

AL showed the strongest anti-oxidant activity in the cellular in-vitro experimental system, in a dose dependent manner (FIG. 2B). As can be seen in FIG. 2C, AO and ASC when measured alone exhibited moderate anti-oxidant activity (6.8% and 9.2% respectively), but together showed a synergistic activity (25%) when measured at concentrations of 100 and 5 µg/ml, respectively)

Example 3: Anti-Inflammatory Evaluation (IL6 Inhibition) of AO, AL, ASC Upon LPS Stimulation FIGS. 3A, 3B and 3C show the anti-inflammatory efficacy in HaCaT cells following treatment with AO, AL, ASC and their combinations. HaCaT cells were seeded and treated with LPS (1 µg/ml) with or without the single Test Items and mixtures. Following 24 hours, IL-6 levels were measured by using commercial kit. The effect of LPS on negative and positive controls is exhibited on graphs. IL-6 levels in the presence of AO (A), AL (B), ASC (C) are presented as Mean±SEM; n=3.

Strong anti-inflammatory activity of the compounds, especially AO and ASC even in comparison to steroid (Dexamethasone) when administrating of AO at concentrations of 10-100 µg/ml and administration of ASC at concentrations of 0.5-5 µg/ml. No synergistic effect of the complex/mixture was shown when combining the compounds together (data not shown).

Example 4: Evaluation of the Anti-Inflammatory Efficacy (IL6 Inhibition) of AO, AL, ASC and their Mixtures in Keratinocytes (HaCaT) Cells Following UVB Irradiation FIG. 4: the efficacy of the Test Items (AO, AL, ASC and their mixtures) to inhibit pro-inflammatory-cytokine secretion (IL-6) in HaCaT cells following exposure to UVB was measured. HaCaT cells were incubated with the Test Items (AO, AL, ASC and their mixtures) for 24 hours, followed by exposure to UVB irradiation (20 mJ/cm2). PABA was used as a positive control and was added 15 min prior to irradiation. The levels of IL-6 and was measured in the spent media by using commercial kits. Results are presented in Mean±SEM; n=3. p<0.05 for differences from the control group.

Figure 4D:
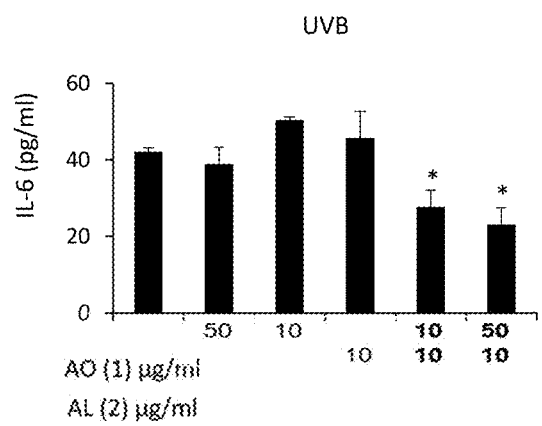

As can be seen from FIG. 4D, AO10 µg/ml or AL10 µg/ml didn't exhibit any inhibition of IL6 following UV radiation in HaCaT cells. However, when the two extracts were added together at the same amount (AO10 µg/ml and AL10 µg/ml) a strong effect of 34.2% inhibition was observed.

Furthermore, when HaCaT cells were incubated with AO50 µg/ml only 7% inhibition of IL6 was observed following UV radiation. When cells were incubated with AL10 µg/ml no inhibition was observed. However, when the two extracts were added together at the same amount (AO50 µg/ml and AL10 µg/ml) a strong effect of 45.13% inhibition was observed (FIG. 4D).

Figure 4E:
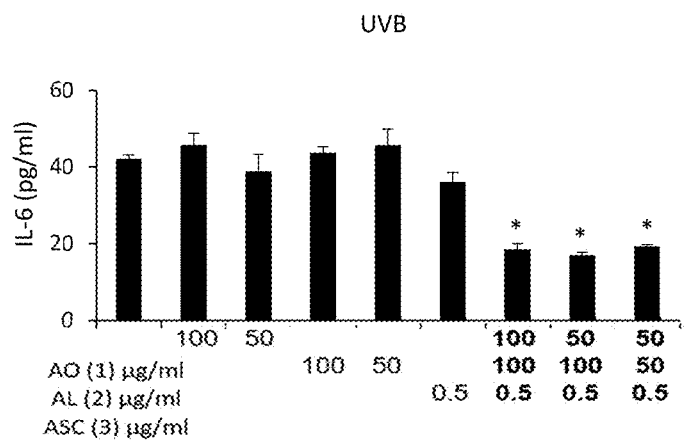
Figure 4F:
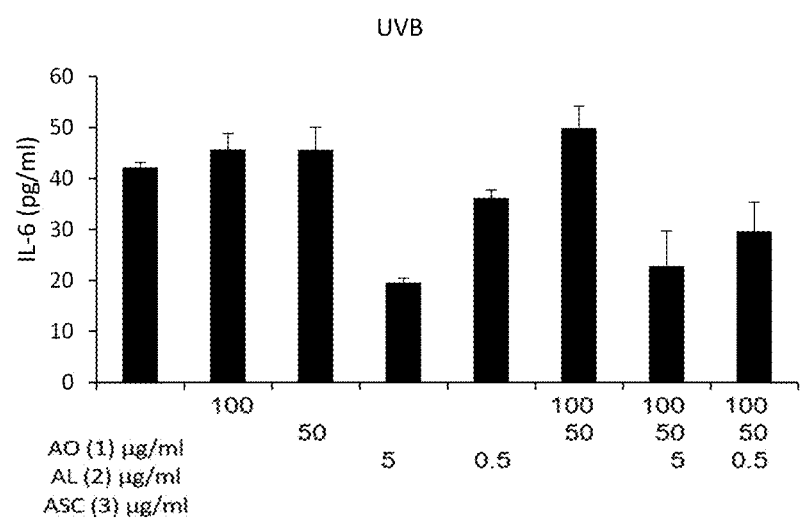

As can be seen from FIG. 4E, AO at 100 µg/ml didn't show any inhibition of IL6. AO at 50 µg/ml showed only very minor effect (7%) following UV radiation in HaCaT cells. AL didn't exhibit any effect on IL6 inhibition at 50 or 100 μg/ml. ASC at 0.5 μg/ml showed only minor effect of 14% IL6 inhibition. However, when the three extracts were added together at the same amount a strong effect of 54-59.85% IL6 inhibition was showed (see table 1-3 and FIG. 4E). This effect was much stronger than each of the compounds alone and also stronger from the effect showed by mixing only two ingredients together (FIG. 4 D).

Synergistic Activity of AO, AL and ASC at Different Concentrations:

As can be clearly seen from Tables 4-6 below and FIG. 4E, the combination of AO, AL and ASC led to a strong synergistic inhibition of IL6 in HaCaT cells following UV radiation suggesting that the complex of the 3 TIs (AO, AL and ASC) could be efficient in preventing photoaging, UV skin damage, preventing skin aging and the formation of skin wrinkles, reduce collagen loss following UV exposure and reduce UV-induced inflammation and inflammation involved sebaceous glands related to acne inflammation.

TABLE 4

| Extract | Concentration (μg/ml) | Inhibition (%) |
| --- | --- | --- |
| AO | 100 | NO |
| AL | 100 | NO |
| ASC | 0.5 | 14 |
| AO + AL + ASC | 100, 100, 0.5 (respectively) | 55.82 |

TABLE 5

| Extract | Concentration (μg/ml) | Inhibition (%) |
| --- | --- | --- |
| AO | 50 | 7 |
| AL | 100 | NO |
| ASC | 0.5 | 14 |
| AO + AL + ASC | 100, 100, 0.5 (respectively) | 59.85 |

TABLE 6

| Extract | Concentration (μg/ml) | Inhibition (%) |
| --- | --- | --- |
| AO | 50 | 7 |
| AL | 50 | NO |
| ASC | 0.5 | 14 |
| AO + AL + ASC | 50, 50, 0.5 (respectively) | 54.1 |

OTHER EXAMPLES

1. After sun: Test items (AO, AL, ASC) and their combinations are tested in-vitro/ex-vivo for their ability to reduce UV damage following UV exposure:

The ability of the TIs and their combinations to reduce DNA damage or to stimulate DNA repair following UV radiation is measured by Commet assay and/or CPD DNA damage.

The ability of the TIs and their mixtures to reduced UV induced ROS generation will be measured.

2. acne in-vitro: ability of TIs and their mixtures to inhibit *p. acnes* in-vitro.

3. Acne Clinical test: efficacy evaluation of an acne treatment using the concentrations of AO: AL: ASC according to the ratio described herein on healthy volunteers with adults acne.

The study duration will be 4 weeks. Evaluations will be made at the following intervals by a Board-Certified Dermatologist on baseline, 2 weeks and 4 weeks. The examination will include Individual Global Counts for: closed comedones, open comedones, papules, pustules, total lesions. Grading of erythema, skin dryness, oiliness and subject post treatment responses. Sebum reduction will be measured by sebumetry.

4. Moisturizing effect: the TIs and their mixtures will be tested as part of a cream on volunteers for their ability to reduces trans epidermal water loss (TEWL) and to elevate skin hydration.

5. Clinical tests: the TIs and their mixtures will be tested as part of a cream for their ability to:
Elevate skin elasticity and firmness
Sebum reduction will be measured by sebumetry.
Reduce wrinkles
Reduced skin thickness
Elevate Skin fatigue resistance
Reduce irritation of SDS/UV
Enhance the efficacy of SPF (will be measured in-vitro/ex-vivo or by a clinical test)

What is claimed is:

1. An emulsion having synergistic interleukin 6 inhibition comprising argan kernel oil, wherein the argan kernel oil is a cold pressed extract from kernel, argania *spinosa* leaf extract wherein the argania *spinosa* was extracted with water and/or glycerin; and Argania *spinosa* sprout cell culture extract that contains 50% of argania *spinosa* stem cell culture with isomalt, lecithin, sodium benzoate and water.

2. The emulsion of claim 1, wherein the argan kernel oil, argan leaf extract and argan stem cells form a complex.

3. The emulsion of claim 1, for treating a dermatological condition in a human.

4. The emulsion of claim 3, wherein the dermatological condition is selected from the group consisting of ultraviolet radiation-induced skin damage, acne, atopic dermatitis, eczema, psoriasis, seborrhea, rocacea and combinations thereof.

5. The emulsion of claim 1, wherein the combination of at least two of argan kernel oil, argan leaf extract, and argan stem cells has an antioxidative synergistic activity.

6. The emulsion of claim 5, wherein the combination of argan kernel oil and argan stem cells has an antioxidative synergistic activity.

7. The emulsion of claim 1, wherein the combination of at least two of argan kernel oil, argan leaf extract, and argan stem cells has an anti-inflammatory synergistic activity.

8. The emulsion of claim 7, for daily use by the human.

9. The emulsion of claim 1, wherein the ratio between argan kernel oil to argan leaf extract is about 1:1 and the ratio between argan kernel oil and argan stem cells is 1:0.001 to 1:0.2.

10. The emulsion of claim 1, wherein the ratio between argan kernel oil to argan leaf extract is about 1:1.

11. The emulsion of claim 1, wherein the argan stem cell levels are between about 0.001%-1%.

12. A method of treating one or more of ultraviolet radiation-induced skin damage, acne, atopic dermatitis, eczema, psoriasis, seborrhea and rosacea, in a human in need thereof comprising contacting the human's skin with the emulsion of claim 1.

13. The method of claim 12, wherein the contacting of the human's skin with the emulsion is performed before, during and/or after the exposure to ultraviolet radiation.

14. The method of claim 12, wherein the human is an athlete.

* * * * *